United States Patent [19]
Podell et al.

[11] Patent Number: 5,419,913
[45] Date of Patent: May 30, 1995

[54] ADHESIVE BANDAGES, WOUND DRESSINGS, SUTURES, DRAPES, ORTHODONTIC RUBBER BANDS, TOOTHBRUSHES, AND THE LIKE

[76] Inventors: Howard I. Podell, 28 Beachfront La., New Rochelle, N.Y. 10853; David L. Podell, Jr., 1100 Park Ave., New York, N.Y. 10021; Albert Goldstein, 87 Glenwood Dr., Tinton Falls, N.J. 07724

[21] Appl. No.: 846,549

[22] Filed: Mar. 5, 1992

[51] Int. Cl.⁶ .................................. A61F 13/00
[52] U.S. Cl. ............................ 424/448; 424/443; 424/445; 424/447; 428/343; 428/354; 602/43; 602/48; 602/54; 602/58; 602/63; 602/77; 128/849; 604/308
[58] Field of Search ............... 424/448, 443, 444, 445, 424/446; 602/42, 57; 428/492, 494, 496, 343

[56] References Cited

U.S. PATENT DOCUMENTS

| | | | |
|---|---|---|---|
| 2,976,576 | 3/1961 | Wichterle | 18/58 |
| 3,419,562 | 12/1968 | Wakeman et al. | 260/286 |
| 3,520,949 | 7/1970 | Shepherd et al. | 260/857 |
| 3,566,874 | 3/1971 | Shepherd et al. | 128/349 |
| 3,574,822 | 4/1971 | Shepherd et al. | 424/47 |
| 3,577,516 | 5/1971 | Gould et al. | 424/46 |
| 3,621,079 | 11/1971 | Leeds | 260/885 |
| 3,632,514 | 1/1972 | Blocher | 252/88 |
| 3,695,921 | 10/1972 | Shepherd et al. | 117/72 |
| 3,813,695 | 6/1974 | Podell, Jr. et al. | 2/168 |
| 4,251,305 | 2/1981 | Becker et al. | 156/86 |
| 4,459,289 | 7/1984 | Maltz | 424/180 |
| 4,485,092 | 11/1984 | Ashton et al. | 424/69 |
| 4,499,154 | 2/1985 | James et al. | 428/494 |
| 4,526,828 | 7/1985 | Fogt et al. | 428/229 |
| 4,548,844 | 10/1985 | Podell et al. | 428/35 |
| 4,575,476 | 3/1986 | Podell et al. | 428/494 |
| 4,589,873 | 5/1986 | Schwartz et al. | 604/265 |
| 4,597,108 | 7/1986 | Momose | 2/168 |
| 4,638,043 | 1/1987 | Szycher et al. | 424/449 |
| 4,747,845 | 5/1988 | Korol | 424/487 |
| 4,846,164 | 7/1989 | Martz | 128/155 |
| 4,857,334 | 8/1989 | Korol | 424/487 |
| 4,867,174 | 9/1989 | Skribiski | 128/772 |
| 4,909,244 | 3/1990 | Quarfoot | 128/156 |
| 4,925,677 | 5/1990 | Feijen | 424/484 |
| 5,059,424 | 10/1991 | Cartmell | 424/443 |

FOREIGN PATENT DOCUMENTS
1200106  7/1970  United Kingdom.

OTHER PUBLICATIONS
"A New Biomaterial for the Control of Infection in the Burn Wound," by P. Nathan et al., vol. XXII, Trans. Amer. Soc. Artif. Int. Organs, 1976.

*Primary Examiner*—D. Gabrielle Phelan
*Attorney, Agent, or Firm*—David P. Gordon

[57] ABSTRACT

An adhesive bandage, wound dressing, suture-like mechanism, or surgical drape for use over a wound is made from a laminate structure of flexible rubber, a hydrophilic hydrogel polymer bonded to one side of the flexible rubber, and an adhesive bonded to the hydrophilic hydrogel polymer along at least a first section of the adhesive bandage, wound dressing, suture-like mechanism, or surgical drape. The adhesive is preferably a hydrogel adhesive with a cellulosic, polyurethane or polyacrylate base, while the flexible rubber is preferably rubber which is pretreated with hydrogel polymer prior to curing. A medicament such as CPC or BAK can be bonded to the hydrophilic hydrogel polymer along the non-adhesive portion of the adhesive bandage, wound dressing or surgical drape to provide slow release medication, and if desired, removable plastic may be provided to cover the adhesive portions. The bandage, wound dressing, suture-like mechanism, or surgical drape may take various shapes, sizes, and arrangements. Orthodontic rubber bands, toothbrushes, dental floss and sutures are also disclosed having a similar arrangement except that the flexible rubber in the case of the toothbrush, dental floss and suture is replaced with bristles, floss thread, and suture thread, and a preferably slow-release medicament is applied to the hydrophilic hydrogel polymer instead of an adhesive.

27 Claims, 2 Drawing Sheets

ADHESIVE BANDAGES, WOUND DRESSINGS, SUTURES, DRAPES, ORTHODONTIC RUBBER BANDS, TOOTHBRUSHES, AND THE LIKE

BACKGROUND OF THE INVENTION

1. Field of the Invention

This invention relates to adhesive bandages, wound dressings, sutures and suture-like mechanisms, surgical drapes, orthodontic rubber bands, and toothbrushes. More particularly, this invention relates to hypoallergenic laminated adhesive bandages, wound dressings, suture-like mechanisms, and drapes, and to medicament releasing orthodontic rubber bands, toothbrushes and sutures.

2. Description of the Prior Art

Adhesive bandages, wound dressings and surgical drapes have been known in the art for some time. Typically, the adhesive bandages include a flexible perforated plastic strip, to which adhesives are bonded on either end of the inside surface, with the adhesive covered by a self-peeling flat strip of sheet material. Gauze is typically located in the middle of the plastic strip between the adhesive sections, with a perforated plastic covering the gauze and attached to the plastic strip.

Recently, the use of a medicated gauze section as part of an adhesive bandage has been introduced to the art, where the adhesive sections of the adhesive bandages are protected by peelable plastic strips which are removed at the time of use. The medicated adhesive bandage is applied so that the gauze section covers the wound area, while the adjoining adhesive sections maintain contact with the skin around the wound. It has been found, however, that the adhesive bandages of the art are troublesome in that the adhesive on the plastic is often a source of irritant to the skin. The bandage does not flex readily, and as a result, not only do they not effectively protect joints, but in covering the skin, each movement of the skin relative to the bandage can result in irritation to the covered skin. Moreover, bandages are often relatively bulky and not easily worn on the foot or toes.

The wound dressings of the art are similar in many respects to the adhesive bandages, except that often the gauze section is much larger than that of the adhesive bandage. Also, typically, more than one plastic adhesive strip is utilized to keep the wound dressing in place. The wound dressings of the art not only suffer from the drawbacks inherent in the adhesive bandages, but they also suffer from the problem of keeping the wound dressing in place. This is particularly so where the wound dressing is utilized to cover a joint, and the joint and skin to which the dressing is applied are subject to movement.

The drapes of the art are typically vinyl sheets with one or more slits located therein and are commonly used to help create a sterile field for surgery. Because of the nature of vinyl, the drapes of the art do not flex in all directions readily, and consequently cannot lie directly adjacent to the skin where the skin surface curves unevenly or in more than one direction. Typically, the drapes of the art do not utilize adhesive sections at all. Moreover, the drapes of the art are subject to the penetration of viruses.

The sutures of the art are typically uncoated cat-gut or synthetic polymer sutures. While helping heal deep wounds by keeping the wounds closed, the sutures themselves are foreign objects which are not always tolerated well by the body. In addition, the process of removing the sutures of the art can cause pain.

Among the patents and publications of interest disclosing bandages, dressings, and the like in the art are: UK #1,200,106 to Harper et al. U.S. Pat. No. 3,520,949 to Shepherd et al. U.S. Pat. No. 3,577,516 to Gould et al. U.S. Pat. No. 4,846,164 to Martz Nathan, P. et al., "A New Biomaterial for the Control of Infection in the Burn Wound" Vol. XXII Trans. Amer. Soc. Artif. Int. Organs, 1976.

Patents disclosing devices such as contact lenses, catheters, surgical gloves, cosmetics, hair lotions, and the like which utilize structures which may be somewhat related to the invention include:

| | |
|---|---|
| UK #1,254,050 to Patent Structures | US #4,251,305 to Becker et al. |
| US #3,419,562 to Wakeman et al. | US #4,458,844 to Podell et al |
| US #3,520,949 to Shepherd et al. | US #4,499,154 to James et al |
| US #3,566,874 to Shepherd et al. | US #4,526,828 to Fogt et al |
| US #3,574,822 to Shepherd et al. | US #4,575,476 to Podell et al |
| US #3,621,079 to Leeds | US #4,597,108 to Momose |
| US #3,695,921 to Shepherd et al | US #4,867,174 to Skribiski |
| US #3,813,695 to Podell et al | |

Finally, other patents of interest include

| | |
|---|---|
| US #2,976,576 to Wichterle et al. | US #4,485,092 to Ashton et al |
| US #3,632,514 to Blocher | US #4,589,873 to Schwartz et al |
| US #4,459,289 to Maltz | US #4,925,677 to Feijen |

The listed patents, while useful in their particular fields, do not provide effective and hypoallergenic adhesive bandages, wound dressings, suture-like mechanisms, and surgical drapes. Neither do they provide sutures or orthodontic rubber bands which promote healing while in place.

SUMMARY OF THE INVENTION

It is therefore an object of the invention to provide adhesive bandages, wound dressings, sutures and suture-like mechanisms, and surgical drapes which are hypoallergenic in nature.

It is a further object of the invention to provide adhesive bandages, wound dressings, sutures and suture-like mechanisms, and surgical drapes which contain bactericides.

It is another object of the invention to provide adhesive bandages, wound dressing, suture-like mechanisms, and drapes which utilize a treated rubber which permits water vapor and oxygen to pass therethrough, without permitting passage of water droplets or microbial agents.

It is yet a further object of the invention to provide adhesive bandages and wound dressings which are completely flexible and which will not accidentally fall off the wound.

It is even another object of the invention to provide adhesive bandages and wound dressings which not only protect and medicate, but which close the wound by applying tension to opposing wound surfaces.

Yet other objects of the invention are to provide coated sutures which promote healing and coated sutures which contain soluble slow release medicines.

Even further objects of the invention are to provide dental related products such as tooth brushes and orthodontic rubber bands comprised of the same or similar materials to the coated sutures and bandages of the invention.

In accord with the objects of the invention, laminated adhesive bandages, wound dressings, suture-like mechanisms, drapes, and the like are provided and broadly comprise a flexible elastomeric piece on one side of which is bonded a hydrogel polymer coating to which in turn, on at least a first portion, is bonded an adhesive. The adhesive is preferably a hydrogel polymer adhesive. If desired, a bactericide may be fixed to a second portion of the hydrogel polymer coated elastomer.

Preferably, the flexible elastomer used as the base of the adhesive bandage, wound dressing, suture-like mechanism, or drape, is a rubber which is specially treated with a hydrogel polymer prior to curing such that the rubber when cured will permit water vapor to escape therethrough. Also, preferably, the hydrogel which coats the rubber is a hydrophilic hydrogel polymer such as polyvinyl pyrrolidone, polyhydroxyethyl acrylate or methacrylate, polyhydroxypropyl acrylate or methacrylate, and copolymers of these with each other or with acrylic or methacrylic acid, acrylic or methacrylic esters or vinyl pyridine. The hydrogel adhesive is preferably hypoallergenic and uses a cellulosic, polyurethane, or polyacrylate base.

The adhesive bandage or wound dressing may take the form of a flat band strip such as is standard in the art with a center section which is intended to cover a wound and side sections having the adhesive. The adhesive sections are preferably covered by removable peel strips prior to use. The flat band strip may be in the shape of a rectangle, a circle, a barbell (for suture-like mechanisms), or any other desired shape to accomplish desired results. Alternatively, the adhesive bandage or wound dressing may take the form of a tubular piece which is folded back on itself with the resulting bottom section intended to cover the wound, and the section or sections which are folded back and sit atop the back section (i.e. "inside-out") having the adhesive and removable strips. The strips are removed prior to use, and the exposed adhesive sections are rolled up and down the limb so that they face "right-side-in" and keep the bandage or wound dressing in its proper place.

In accord with another aspect of the invention, a suture is provided which shares similarities to the laminated adhesive bandages of the invention. The suture is comprised of a flexible natural (e.g., cat-gut) or synthetic (e.g., any of numerous synthetic polymers) thread to which is bonded a hydrogel polymer coating. Preferably, the surface of the suture is activated and a soluble medicine such as a bactericide added to the hydrogel polymer coated elastomer.

In accord with a further aspect of the invention, orthodontic rubber bands which share similarities to the laminated adhesive bandages and the sutures of the invention are provided. The rubber bands are comprised of a flexible elastomeric band to which is bonded a hydrogel polymer coating. A soluble medicine such as a bactericide is fixed to the hydrogel polymer coated elastomer. If desired, the soluble medicine may be a slow-release medicine. A tooth brush is similarly comprised, except instead of using a flexible elastomeric band, a plurality of bristles comprised of, e.g., nylon, are used and are coated with the hydrogel polymer coating and a medicine such as a slow-release bactericide.

A better understanding of the invention, as well as additional objects and advantages of the invention will become apparent to those skilled in the art upon reference to the detailed description and the accompanying drawings.

BRIEF DESCRIPTION OF THE DRAWINGS

FIG. 1b is a cross section through the invention shown in FIG. 1a;

DETAILED DESCRIPTION OF THE PREFERRED EMBODIMENT

Figure 1A:
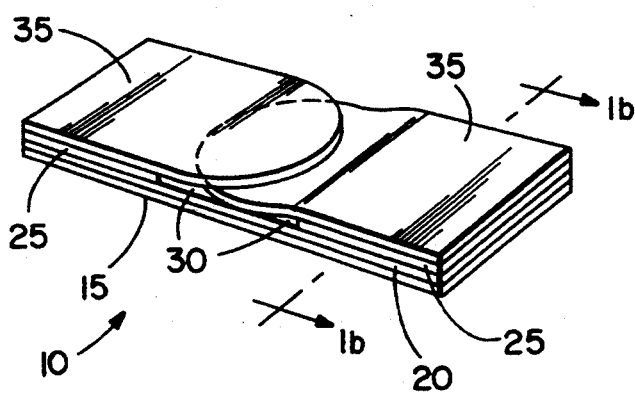
FIG. 1a is a perspective view of an adhesive bandage, wound dressing, or drape of the preferred embodiment of the invention.
Figure 1B:
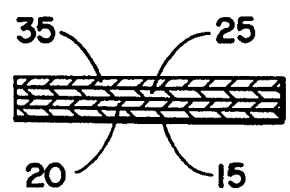

Turning to FIGS. 1a and 1b, one embodiment of an adhesive bandage, wound dressing, suture-like mechanism, drape 10 or the like is shown. For purposes herein, only an adhesive bandage will be referred to, although it will be recognized that the description applies equally to a wound dressing, suture-like mechanism, or drape. As shown, the adhesive bandage 10 is a laminate comprised of a flexible elastomer 15 to which on one side is bonded a hydrogel polymer coating 20. The flexible elastomer 15 is preferably a treated rubber which permits water vapor and/or oxygen vapor to perfuse therethrough, although, if desired, any natural or synthetic rubber (including latex) may be used. The preferred perfusable rubber can be obtained by adding a hydrogel polymer to a natural rubber base before the rubber base is vulcanized. The hydrogel polymer coating 20 which completely coats one side of the flexible elastomer 15 is preferably a hydrophilic hydrogel polymer such as polyvinyl pyrrolidone, polyhydroxyethyl acrylate or methacrylate, polyhydroxypropyl acrylate or methacrylate, and copolymers of these with each other or with acrylic or methacrylic acid, acrylic or methacrylic esters or vinyl pyridine, although other suitable hydrogel polymers can be used. The hydrogel polymer coating 20 is bonded to the flexible elastomer in manners well known in the art.

Bonded to at least certain sections of the hydrogel polymer coating 20 is an adhesive 25. The adhesive is preferably a hypoallergenic hydrogel adhesive which uses a cellulosic, polyurethane, or polyacrylate 30 base. Again, the adhesive is bonded to the hydrogel polymer coating in well known manners. Optionally, a medicament 30 which is bondable to the hydrogel polymer coating 20 is bonded at desired locations. If desired, in fact, the medicament 30 can be mixed with the hydrogel adhesive 25. Preferred medicament include quaternary ammonium compounds such as cetyl pyridium chloride (CPC) or Benzyl Ammonium (BAK) which are both surfactants and bactericides. When bonded to the hydrogel coating, by heating and drying a dilute solution of the quaternary ammonium compound onto the hydrogel coating, the resulting structure allows bactericide to slowly release onto a surface, such as skin or a wounded area of skin, which is in intimate contact with the coating 20. Similarly, a chemical encompassing wound healing factors may also be fixed into the hydrogel coating so as to slowly release onto a wound which is covered by the adhesive bandage 10.

In order to protect the adhesive bandage 10 from contamination, removable plastic peel strips 35 may be provided. The plastic peel strips 35 removably adhere to the adhesive 25, but do not substantially remove either the adhesive 25 or the medicament 30 when they are removed just prior to use of the adhesive bandage 10.

Figure 2A:
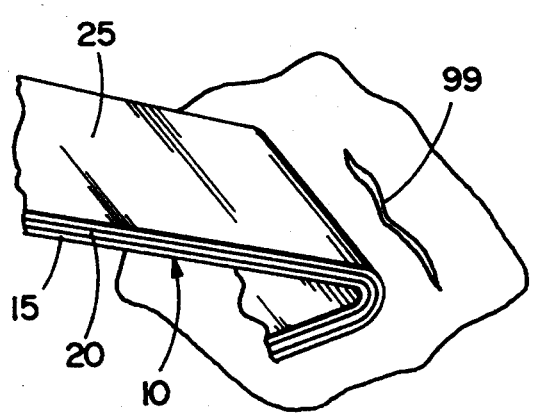
FIG. 2a is a perspective view of an alternative embodiment of the adhesive bandage as partially applied to a wound area.
Figure 2B:
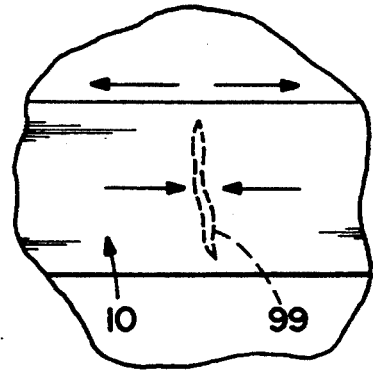
FIG. 2b is a diagrammatic view of the adhesive bandage of FIG. 2a in use, showing forces applied by the adhesive bandage to the wound area.

While the adhesive bandage of FIG. 1 takes the form of a flat strip such as is standard in the art with a center section which is intended to cover a wound and side sections having the adhesive, it will be recognized that the size and shape of the adhesive bandage, and the relative size of the adhesive coated area and area not coated by the adhesive may vary considerably as desired. For example, and not by way of limitation, an adhesive bandage may take the shape of a rectangle, a square, a circle, an oval, a barbell (as is discussed hereinafter relative to FIG. 4), etc. Also by way of example and not limitation, the adhesive 25 may be placed around the entire circumference of the adhesive bandage leaving a central area which has the hydrogel polymer or medicament exposed, or the adhesive 25 may be placed on two sections of the bandage with a middle section separating the two sections having the hydrogel polymer or medicament exposed. Alternatively, the adhesive may cover the entire area of the bandage as indicated in FIG. 2a, so as to cover the wound area to which it is applied. In this manner, the adhesive bandage 10 provides tension and serves to draw the opposed skin surfaces adjacent a wounded area 99 together to close the wound area as indicated in FIG. 2b.

Figure 3B:
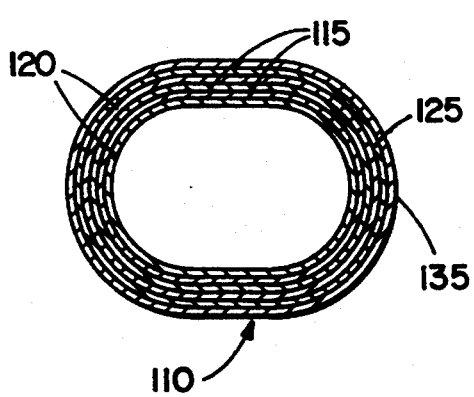
FIG. 3b is a cross section through the alternative preferred embodiment of the invention shown in FIG. 2a while in use.
Figure 3A:
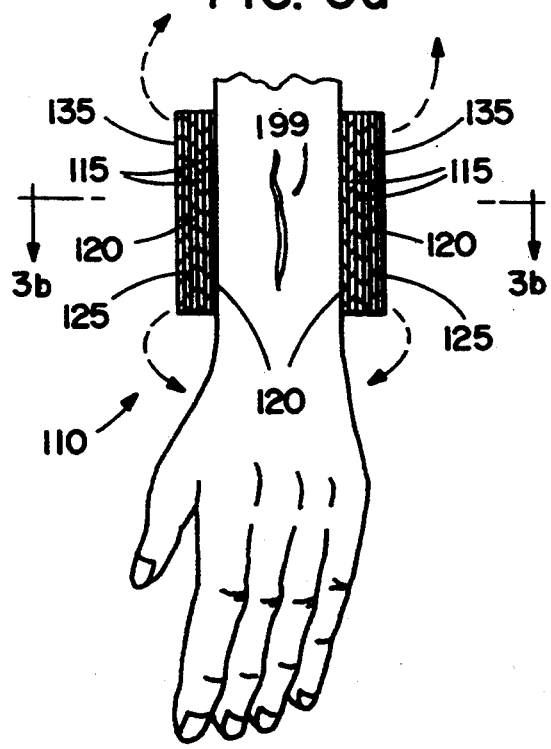
FIG. 3a is a perspective view of an alternative preferred embodiment of the adhesive bandage or wound dressing invention.

Turning to FIGS. 3a and 3b, another arrangement for an adhesive bandage or wound dressing is shown (for purposes of FIGS. 3a and 3b the invention will be described as a wound dressing). The wound dressing 110 is in the form of a laminated tube comprised of a flexible elastomer 115 to which on one side is bonded a hydrogel polymer coating 120. The flexible elastomer 115 and the hydrogel polymer coating 120 are as described above with reference to FIGS. 1a and 1b. As shown in FIGS. 3a and 3b, prior to use, the wound dressing is folded back on itself such that taken in order from the skin or wound outward, layers of hydrogel polymer coating 120, flexible elastomer 115, flexible elastomer 115, and hydrogel polymer coating 120 are seen. If desired, a medicament (not shown) may be bonded to the hydrogel polymer coating where the wound dressing 110 is to contact the skin wound 199.

Bonded to the hydrogel polymer coating 120 at the folded back areas of the wound dressing 110 is an adhesive 125 as disclosed with reference to FIG. 1a and 1b. In order to protect the wound dressing 110 from contamination and to help expedite the use of the wound dressing 110, removable plastic peel strips 135 may be provided over the adhesive.

In using the wound dressing 110, the entire assembly is slid over the digit or limb having the wound until the wound is covered by the medicament or the exposed hydrogel polymer coating 120. The removable plastic strips 135 are then removed from the adhesive 125, and the folded back section or sections of the wound dressing 110 having (from outside in) the adhesive 125, the hydrogel polymer 120, and the flexible elastomer 115 are turned "right-side-in" (i.e. they are rolled over themselves). Once the folded back sections are turned right-side-in, the adhesive 125 contacts the skin and holds the wound dressing 110 in place.

It has been found that the tension of the flexible elastomer 115, and particularly the tension of rubber, causes the wound to close quickly and neatly (as indicated in FIGS. 2a and 2b). Also, particularly where the rubber is perfusable, the wound tends to heal more quickly than would otherwise happen with standard wound dressings. Further, the elastomeric nature of the base material, particularly where natural perfusable rubber is utilized, enables the bandage to conform to irregularities of shape of the member to which applied, thereby permitting movement of the covered extensor and flexor skin surfaces and including free movement of any joints that are covered by the bandage. In fact, among other places, the provided bandages are used advantageously on feet and toes. Additional advantage is gained by the fact that the hydrogel polymer (and medicament) coating adheres to the flexible elastomer even when the elastomer stretches.

Figure 4:
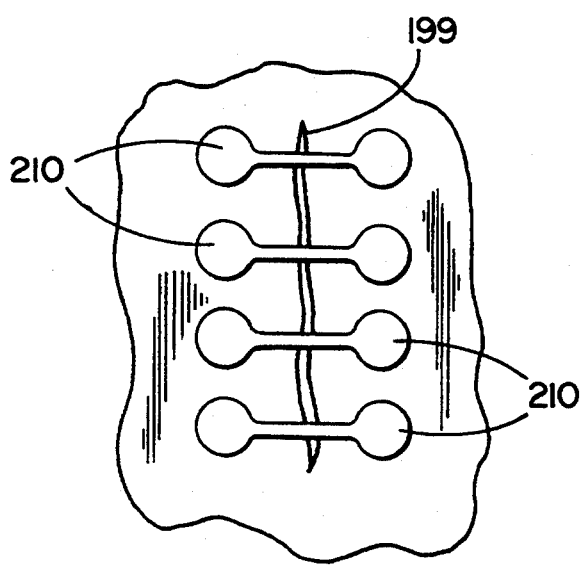
FIG. 4 is a diagrammatic view of the suture-like mechanism embodiment of the invention in use.

For many minor wounds or surgical openings, a bandage of the invention may be employed as a suture means as indicated in FIG. 4, instead of, or complementary with, conventional sutures or staples. Because the skin sutures 210 are elastomeric in nature, if they are stretched prior to application across wound 199, they can apply the necessary tension forces (see FIG. 2b) required to close and maintain together the edges of the skin adjacent to the wound 199.

It will be appreciated that the use of the laminated structure disclosed above with reference to adhesive bandages, wound dressings, and skin sutures, is of particular advantage in use as a surgical drape for many reasons (some of which are identical to the advantages of the other embodiments). First, a sterile field may be established to which the drape will adhere. Second, the laminated structure may be easily cut open to reveal the area upon which surgery is to be conducted. Third, an opening in the laminated structure or the external shape of the drape may be easily cut to desired size. Fourth, the antiseptic nature of the hydrogel surface of the surgical drape contacting the skin of the patient prevents cross-infection from the skin surface to the wound area and vice-versa. This antiseptic coating prevents regrowth of bacteria on the skin surfaces covered by the surgical drape during the operation.

Figure 5:
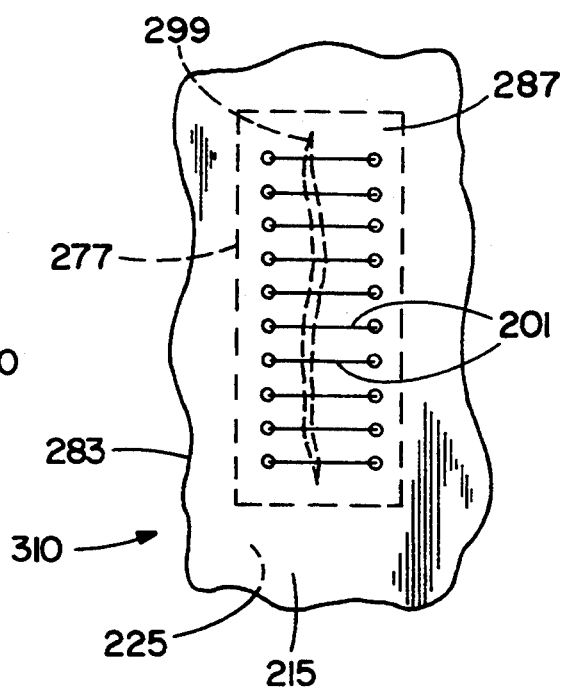
FIG. 5 is a diagrammatic view of a portion of the drape embodiment of the invention in use.

As seen in FIG. 5, an operation wound 299 is sutured by conventional stitches or staples 201 which are sewn or stapled through drape 310 which is left in place upon completion of the operation. The drape 310 is cut by the surgeon along dash lines 277 which is the periphery of the sewn area. In this manner, the large excess drape outer portion 283 of the drape 310 is removed, and the smaller inner portion 287 directly around the stitches 201 is left in place until the wound 299 heals and the stitches 201 are removed. With the crossing sections of the stitches not in direct contact with the wound area, the cosmetic scars from the stitches or staples will be largely eliminated. Meanwhile, the bactericide agent in the hydrogel and adhesive undercoating 225 of the drape prevents regrowth of bacteria on the skin under portion 287, and thereby prevents (re)infection. Also, the elastomeric properties of the rubber drape permit the drape to lie against the skin without end forces that would interfere with normal movement of the sewn area. Thus, the sutures are not restricted, and the healing of the wound may proceeds without medicament.

Figure 6:
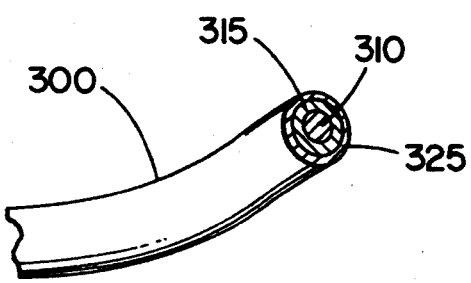
FIG. 6 is a cross section through the preferred embodiment of the suture of the invention, the bristles of the toothbrush of the invention having an identically appearing cross-section.

Turning to FIG. 6, a cross-section through a suture 300 of the invention is seen. The suture 300 is comprised of a flexible natural (e.g., cat-gut) or synthetic (e.g., any of numerous synthetic polymers such as nylon) thread 310 (i.e., a standard suture) to which is bonded a hydrogel polymer coating 315. Bonded in turn to the hydrogel polymer coating 315 is preferably a bactericide or medicine 325. The bactericide 325 is bonded to the hydrogel polymer coating by activating the surface of the hydrogel polymer by corona discharge or via chemical priming such as by the use of, e.g., hydrochloric acid, sulfuric acid, or nitric acid. The suture 300 of FIG. 6 is advantageous in that it presents a surface which aids the healing process as well as being easily removed. In addition, since the hydrogel surface becomes tacky in the presence of moisture, the suture material will stick to itself, and the suture knot, rather than being slippery, will hold well. Also, if desired, the bactericide or medicine 325 can be a slow-release medicine so that the medicine dose is released during the entire effective use of the suture 300.

In accord with another aspect of the invention, a new toothbrush arrangement and a new dental floss arrangement are provided which have the same arrangement as the suture of FIG. 6; that is, in the case of the toothbrush, a bristle is provided in lieu of the thread 310, and the bristle is coated with the hydrogel polymer coating 315 and a bactericide or medicine 325, while in the case of the dental floss, a fibrous string is provided in lieu of the thread, and the string is coated with the hydrogel polymer coating and a bactericide or medicine 325. In the case of the dental floss, the bactericide or medicine is preferably released on contact with moisture and/or by rubbing, while in the case of the toothbrush, the medicine 325 is preferably a slow-release medicine. In fact, in the case of the toothbrush, the medicine 325 is preferably released over at least thirty days, and preferably between thirty and ninety days.

Figure 7:
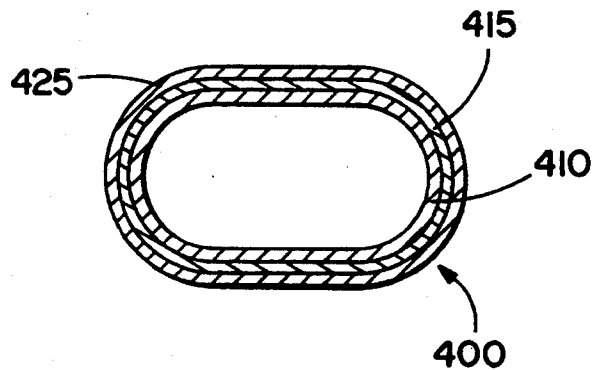
FIG. 7 is a longitudinal cross section through the preferred rubber band of the invention.

Turning to FIG. 7, a new orthodontic rubber band 400 is provided which generally has the same arrangement as the suture (and toothbrush) of FIG. 6. The rubber band 400 is comprised of a flexible elastomeric material such as rubber or latex to which is bonded a hydrogel polymer coating 415. Bonded in turn to the hydrogel polymer coating 415 is preferably a bactericide or medicine 425, which, if desired, can be a slow-release medicine. The rubber band 400 of FIG. 7 is advantageous in that it presents a surface which can be help heal gingivitis or other gum inflammations or diseases as well as preventing the inflammations or diseases if none are present.

There has been described and illustrated herein hypoallergenic laminated adhesive bandages, wound dressings, suture-like mechanisms, surgical drapes, sutures, orthodontic rubber bands, toothbrushes, dental floss and the like. While particular embodiments have been described, it is not intended that the invention be limited thereto, as it is intended that the invention be as broad in scope as the art will allow. Thus, for example, while particular hydrogel coatings and medicaments were listed as being advantageous, it will be appreciated that other hydrogel coatings and medicaments could be utilized. Also, while particular arrangements (e.g. rectangular strips, tubes) were shown, the laminated bandages, dressings, etc., could take other forms as desired such as a tube with sections cut out, etc. for particular types or shapes of wounds. Further, the laminated structure of the invention can be used in other environments such as in the mouth as a dental dam, and it is not intended that the invention be limited to only the end uses particularly disclosed, except that it be used in conjunction with a "wound" site. Therefore, it will be appreciated by those skilled in the art that yet other modifications could be made to the provided invention with deviating from its spirit and scope as so claimed.

We claim:

1. An adhesive bandage, wound dressing, surgical drape, or suture means for use over a wound, comprising a laminate structure of:
   a) a piece of elastic flexible elastomer which when applied over a wound provides tension which acts to close the wound;
   b) a hydrophilic hydrogel polymer bonded to at least one side of said elastic flexible elastomer, said hydrophilic hydrogel polymer adhering to said elastic flexible elastomer when said flexible elastomer stretches such that said hydrophilic hydrogel polymer is in held in contact with the wound by said piece of elastic flexible elastomer which conforms to irregularities in surface shade around the wound; and
   c) an adhesive bonded to said hydrophilic hydrogel polymer along at least a first section of said adhesive bandage, wound dressing, surgical drape, or suture means.

2. An adhesive bandage, wound dressing, surgical drape, or suture means according to claim 1, further comprising:
   d) a medicament bonded to said hydrophilic hydrogel polymer along at least a second section of said adhesive bandage, wound dressing, suture means, or surgical drape.

3. An adhesive bandage, wound dressing, surgical drape, or suture means according to claim 1, further comprising:
   d) at least one removable plastic covering for attachment to at least a portion of said adhesive.

4. An adhesive bandage, wound dressing, surgical drape, or suture means according to claim 2, further comprising:
   e) at least one removable plastic covering for attachment to at least a portion of said adhesive.

5. An adhesive bandage, wound dressing, surgical drape, or suture means according to claim 1, wherein:
   said flexible elastomer is a natural or synthetic rubber.

6. An adhesive bandage, wound dressing, surgical drape, or suture means according to claim 5, wherein:
   said flexible elastomer is a perfusible rubber.

7. An adhesive bandage, wound dressing, surgical drape, or suture means according to claim 1, wherein:
   said adhesive is a hypoallergenic hydrogel adhesive.

8. An adhesive bandage, wound dressing, surgical drape, or suture means according to claim 7, wherein:

said hypoallergenic hydrogel adhesive has a cellulosic, polyurethane, or polyacrylate base.

9. An adhesive bandage, wound dressing, surgical drape, or suture means according to claim 2, wherein: said medicament is a bactericide.

10. An adhesive bandage, wound dressing, surgical drape, or suture means according to claim 2, wherein: said medicament is one of a quaternary ammonium compound.

11. An adhesive bandage, wound dressing, surgical drape, or suture means according to claim 1, wherein: said flexible elastomer is in the shape of a parallelogram, said parallelogram being divided into a first quadrilateral, a middle quadrilateral, and a second quadrilateral, said first and second quadrilaterals having said adhesive and said middle quadrilateral without said adhesive.

12. An adhesive bandage, wound dressing, surgical drape, or suture means according to claim 11, further comprising:
d) a medicament bonded to said hydrophilic hydrogel polymer along at least a portion of said middle quadrilateral.

13. An adhesive bandage, wound dressing, surgical drape, or suture means according to claim 12, wherein: said medicament is a quaternary ammonium compound.

14. An adhesive bandage, wound dressing, surgical drape, or suture means according to claim 11, further comprising:
d) at least one removable plastic covering for attachment to at least adhesive.

15. An adhesive bandage, wound dressing, surgical drape, or suture means according to claim 1, wherein: said flexible elastomer is in the shape of a tube, said hydrophilic hydrogel polymer being bonded to the inner surface of said flexible elastomer tube.

16. An adhesive bandage, wound dressing, surgical drape, or suture means according to claim 15, wherein: said adhesive bandage, wound dressing, surgical drape, or suture means has a first section and at least one second section folded atop said first section such that from inside to out said adhesive bandage, wound dressing, surgical drape, or suture means has a first section hydrophilic hydrogel polymer bonded to a first section flexible elastomer, a second section flexible elastomer to which a second section hydrophilic hydrogel polymer is bonded, and a second section adhesive which is bonded to the hydrophilic hydrogel polymer.

17. An adhesive bandage, wound dressing, surgical drape, or suture means according to claim 16, further comprising:
d) a medicament bonded to at least a portion of said first section hydrophilic hydrogel polymer.

18. An adhesive bandage, wound dressing, surgical drape, or suture means according to claim 16, further comprising:
d) at least one removable plastic covering for attachment to at least a portion of said adhesive.

19. An adhesive bandage, wound dressing, surgical drape, or suture means according to claim 17, further comprising:
e) at least one removable plastic covering for attachment to at least a portion of said adhesive.

20. An adhesive bandage, wound dressing, surgical drape, or suture means according to claim 1, wherein: said adhesive bonded to said hydrophilic hydrogel polymer is bonded along the entire adhesive bandage, wound dressing, surgical drape, or suture means.

21. An adhesive bandage, wound dressing, surgical drape, suture means according to claim 20, further comprising:
d) a medicament bonded to said hydrophilic hydrogel polymer along at least a portion of said adhesive bandage, wound dressing, surgical drape, or suture means.

22. An adhesive bandage, wound dressing, surgical drape, or suture means according to claim 21, wherein: said medicament is a quaternary ammonium compound.

23. An adhesive bandage, wound dressing, surgical drape, or suture means according to claim 21, further comprising:
e) at least one removable plastic covering for attachment to at least adhesive.

24. An adhesive bandage, wound dressing, surgical drape, or suture means according to claim 1, wherein: said flexible elastomer is in the shape of a barbell with enlarged first and second ends and a narrow strip connecting said enlarged first and second ends, at least said enlarged first and second ends having said adhesive.

25. An adhesive bandage, wound dressing, surgical drape, or suture means according to claim 25, further comprising:
d) a medicament bonded to said hydrophilic hydrogel polymer along at least a portion of said adhesive bandage, wound dressing, surgical drape, or suture means.

26. An adhesive bandage, wound dressing, surgical drape, or suture means according to claim 25, wherein: said medicament is a quaternary ammonium compound or.

27. An adhesive bandage, wound dressing, or surgical drape, for use over a wound, comprising a laminate structure of:
a) a piece of elastic flexible perfusible rubber which when applied over a wound provides tension which acts to close the wound;
b) a hydrophilic hydrogel polymer bonded to at least one side of said flexible perfusible rubber., said hydrophilic hydrogel polymer adhering to said elastic flexible perfusible rubber when said plastic flexible perfusible rubber stretches such that said hydrophilic hydrogel polymer is held in contact with the wound by said piece of elastic flexible elastomer which conforms to irregularities in surface shape around the wound;
c) an adhesive bonded to said hydrophilic hydrogel polymer along at least a first section of said adhesive bandage, wound dressing, or surgical drape;
d) a medicament bonded to said hydrophilic hydrogel polymer along at least a second section of said adhesive bandage, wound dressing or surgical drape, wherein said medicament is held in contact with the wound by said hydrophilic hydrogel polymer when said elastic flexible perfusible rubber stretches over the wound; and
e) at least one removable plastic covering for attachment to at least a portion of said adhesive.

* * * * *